United States Patent [19]

Klochko et al.

[11] 4,452,066

[45] Jun. 5, 1984

[54] DEVICE FOR MEASURING DYNAMIC CHARACTERISTICS OF OBJECTS UNDER IMPACT

[76] Inventors: Viktor A. Klochko, Oktyabrskaya ulitsa, 18, kv. 50; Viktor G. Rygalin, 3 Dorozhny proezd, 5, korpus 2, kv. 103; Dmitry A. Grechinsky, Shipilovsky proezd, 61, korpus 2, kv. 246; Vladimir V. Kljuev, ulitsa Volgina, 44, korpus 13, kv. 69; Vadim N. Kovalsky, Marksistskaya ulitsa, 9, kv. 307, all of Moscow, U.S.S.R.

[21] Appl. No.: 375,029

[22] PCT Filed: Aug. 22, 1980

[86] PCT No.: PCT/SU80/00142

§ 371 Date: Apr. 20, 1982

§ 102(e) Date: Apr. 20, 1982

[87] PCT Pub. No.: WO82/00715

PCT Pub. Date: Mar. 4, 1982

[51] Int. Cl.³ .............................................. G01N 3/30
[52] U.S. Cl. ..................................................... 73/12
[58] Field of Search ............................. 73/574, 12, 11

[56] References Cited

U.S. PATENT DOCUMENTS 4,023,396  5/1977  Yakshin et al. ........................ 73/12
4,030,339  6/1977  Yakshin et al. ........................ 73/12
4,055,842  10/1977 Yakshin et al. ..................... 73/12 X

FOREIGN PATENT DOCUMENTS 1487506  10/1977  United Kingdom .

Primary Examiner—Gerald Goldberg
Assistant Examiner—Brian Tumm
Attorney, Agent, or Firm—Fleit, Jacobson, Cohn & Price

[57] ABSTRACT

A series circuit including a transducer responding to the parameters of motion of an object during impact, a pulse shaper and a main switch. Connected to the output of the switch are a unit for measuring the area of the impact pulse, an integrator and two AND-NOT elements. The device also includes three additional switches. One input of one switch is connected to the output of the area measuring unit and the other input of this switch is connected to the output of one AND-NOT, while the output is connected to the input of a memory block. One input of the second switch is connected to the output of the area measuring unit, while the outer input of this switch is connected to the output of the AND-NOT through a NOT element. The output of the second switch is connected to the input of a second memory block. One input of the third switch is connected to the output of the other AND-NOT and the other input of this switch is connected to the output of the main switch, while the output of the third switch is connected to the control input of the controlled switch and to the input of a trigger. The outputs of the trigger are connected to the second inputs of the memory blocks. The outputs of the memory blocks are connected to the input of an indicator through two squarers and an adder.

1 Claim, 1 Drawing Figure

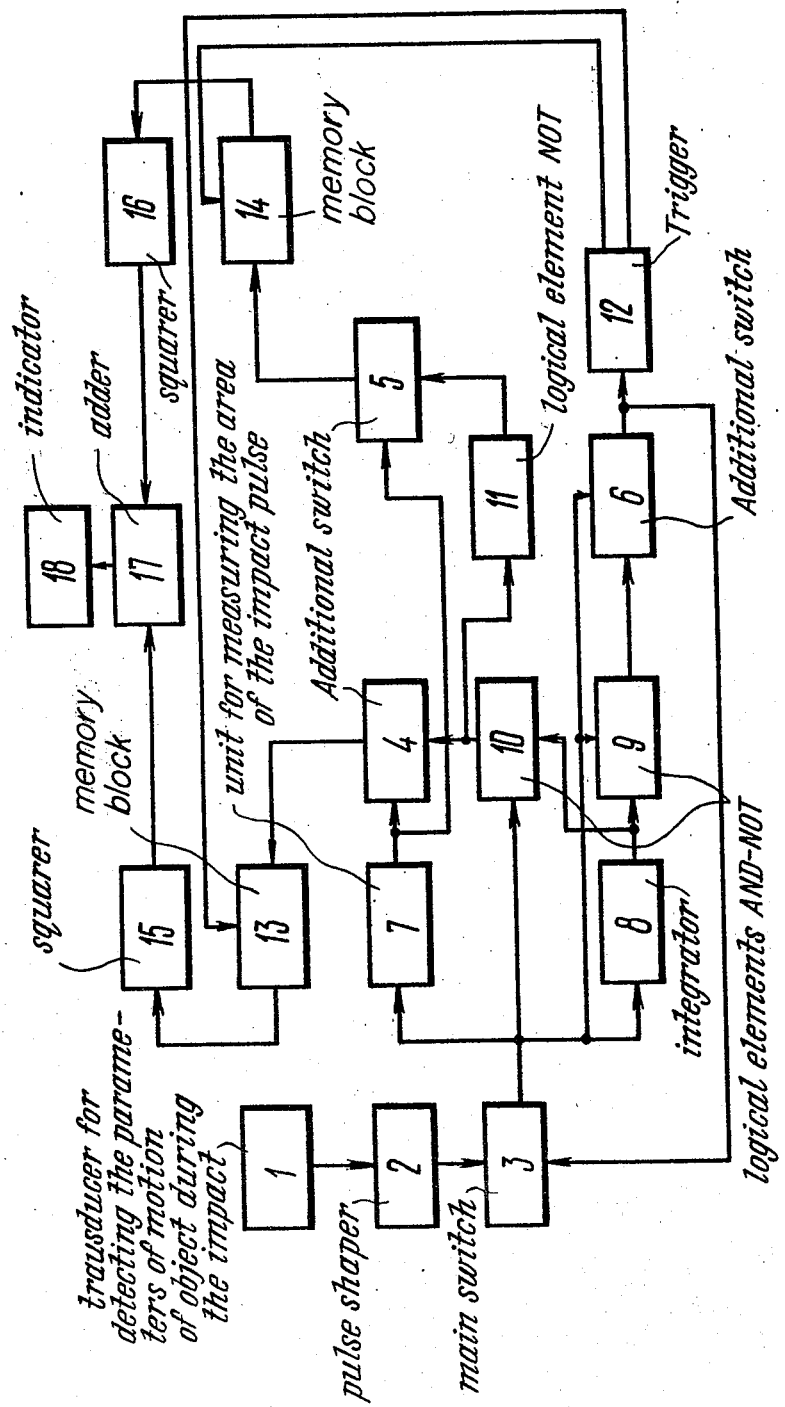

DEVICE FOR MEASURING DYNAMIC CHARACTERISTICS OF OBJECTS UNDER IMPACT

TECHNICAL FIELD

The present invention relates to devices for measuring non-electrical quantities and, more particularly, the invention relates to devices for measuring the dynamic characteristics of objects under impact.

BACKGROUND ART

Known in the art is a device for measuring the parameters of an impact comprising coarse and accurate comparators connected to an integrator, logical inhibition elements, elements AND, OR, shift registers and a digital-to-analog converter (cf. U.S. Pat. No. 3,286,253, cl. 340-347, published in 1966).

The known device makes it possible to measure in a digital form the peak value of impact acceleration and the duration of an impact pulse. However, using this device, it is not possible to measure directly the work of plastic deformation during the impact. This work can only be approximately estimated by studying the shape of the impact pulse. Furthermore, this device is featured by comparatively low accuracy when measuring the peak value of the impact pulse.

Also known in the art is a device for measuring the dynamic characteristics of objects under impact comprising a series circuit consisting of a transducer responding to the parameters of motion of the object during the impact, a pulse shaper and a controlled switch, to the output of which there are connected the inputs of a unit for measuring the area of the impact pulse, an integrator and first and second logical elements AND-NOT. Connected to the second inputs of the logical elements AND-NOT is the integrator output. The output of the first logical element AND-NOT is connected to the input of a logical element NOT whose second input is connected to the output of the unit for measuring the area of the impact pulse. Connected to the output of the second element AND-NOT is a trigger whose second input is connected to the output of the unit for measuring the area of the impact pulse, while the output is connected respectively to the inputs of the first and second memory registers. The second input of the first memory register is connected directly to the output of the unit for measuring the pulse area, the second input of the second memory register is connected to the output of the logical element NOT, while the outputs of the memory registers are connected to the inputs of an indicator (cf. U.S. Pat. No. 4,004,450, cl. 73/12, published in 1977).

This device makes it possible to measure the area of the leading edge of the impact pulse characterizing the velocity of collision of the bodies, the area of the trailing edge of the impact pulse characterizing the velocity of recoil of the colliding bodies and the total power of the impact pulse characterizing the total change in the velocity of the colliding bodies during the impact. Using these data and sophisticated calculations, it is possible to obtain information on the work of plastic deformation during the impact. However, the accuracy of such calculations is rather low and, furthermore, the reliability of such data cannot be guaranteed due to the presence of subjective estimates of the operator. The efficiency of this device is lowered due to the necessity of making complex calculations for determining the work of plastic deformation during the impact.

DISCLOSURE OF THE INVENTION

The basic object of the invention is to develop such a device for measuring the dynamic characteristics of objects under impact, which would provide an automatic supply of quantitative information on the work of plastic deformation during the impact so as to exclude the subjective factor, when estimating the work of plastic deformation, and would contribute to an increase in the accuracy, reliability and efficiency of the measurements.

This object is attained by providing a device for measuring the dynamic characteristics of objects under impact comprising the following units connected in series: a transducer responding to the parameters of motion of the object during the impact, a pulse shaper, a controlled switch whose output is connected to the inputs of a unit for measuring the area of the impact pulse, an integrator and to the first inputs of first and second logical elements AND-NOT whose second inputs are connected to the integrator output; a logical element NOT whose input is connected to the output of the first logical element AND-NOT; a trigger; first and second memory blocks having control inputs connected each to one of the trigger outputs, and an indicator, according to the invention, the device is provided with a first additional controlled switch, one input of which is connected to the output of the area measuring unit and the other input is connected to the output of the first logical element AND-NOT, while the output of this switch is connected to the input of the first memory block; a second additional controlled switch, one input of which is connected to the output of the area measuring unit and the second input is connected to the output of the logical element NOT, the output of said second additional switch being connected to the input of the second memory block; a third additional controlled switch, one input of which is connected to the output of the second element AND-NOT and the other input connected to the output of the main switch, while the output of this switch is connected to the input of the trigger and to the control input of the main switch; first and second squarers whose inputs are connected respectively to the outputs of the first and second memory blocks; and an adder whose inputs are connected to the outputs of said squarers, while the output is connected to the input of the indicator.

The device for measuring the dynamic characteristics of objects under impact made in accordance with this invention, provides automatic supply of quantitative information on the work of plastic deformation of the object under impact to the indicator, is characterized by high accuracy of measurements and operational reliability and makes it possible to considerably increase labor productivity.

BRIEF DESCRIPTION OF THE DRAWING

The invention is further described by way of example with reference to the accompanying drawing, which shows a block diagram of the device for measuring dynamic characteristics of objects under impact, according to the invention.

PREFERABLE EMBODIMENT OF THE INVENTION

The device for measuring the dynamic characteristics of objects under impact comprises a transducer 1 for detecting the parameters of motion of the object during the impact, a pulse shaper 2, a main switch 3, additional switches 4, 5 and 6, a unit 7 for measuring the area of the impact pulse, an integrator 8, logical elements AND-NOT 9 and 10, a logical element NOT 11, a trigger 12, memory blocks 13 and 14, squarers 15 and 16, an adder 17 and an indicator 18.

The transducer 1, which, for example, is a piezoelectric accelerometer, is secured to one of the colliding bodies. The transducer 1 through pulse shaper 2, e.g. a charge preamplifier used for matching the output impedance of the transducer 1 and the following measuring elements of the device and for standardization of the electrical signal from the transducer 1 (impact response), is connected to one input of the switch 3. The switch 3 transmits the signal during the impact and switches off the measuring elements of the device after the impact pulse is over.

The output of the switch 3 is connected to the inputs of the unit 7 for measuring the area, the integrator 8 and to the first inputs of the logical elements AND-NOT 9 and 10.

One input of the controlled switch 4 is connected to the output of the unit 7 for measuring the area, the other input of this switch is connected to the output of the logical element AND-NOT 10, while the output of the switch 4 is connected to the input of the memory block 13.

One input of the controlled switch 5 is also connected to the output of the unit 7 for measuring the area, the other input of this switch is connected to the output of the logical element NOT 11 and the output of the switch 5 is connected to the input of the memory block 14.

The memory blocks 13, 14 through their outputs are connected to the inputs of the squarers 15, 16, respectively, whose outputs are connected to the respective inputs of an adder 17, which, in turn, is connected through its output to the input of an indicator 18.

One input of the controlled switch 6 is connected to the output of the logical element AND-NOT 9, the other input of this switch is connected to the output of the switch 3, while the output of the switch 6 is connected to the control input of the switch 3 and to the input of the trigger 12 whose outputs are connected to the inputs of the memory blocks 13, 14.

The area measuring unit 7 is for example an analog circuit including an integrator connected through its output to a capacitor; the discharge of this capacitor is effected by a constant current and, therefore, the discharge time of the capacitor is proportional to the pulse area and is used for measurement of the areas of the leading and trailing edges of the pulse, the quantitative data of which are recorded into the memory blocks 13 and 14. The logical elements AND-NOT 9 and 10, switches 4, 5, 6 and trigger 12 (e.g. flip-flop or D-trigger) are used for shaping the signals permitting recording of the data of the areas of the leading and trailing edges of the pulses, their computation and substraction of their squares in the adder 17. The quantitative data on the work of plastic deformation during the impact are recorded by a digital indicator 18, whose operating conditions selected by the operator provide direct digital information on the work of plastic deformation.

The device for measuring the dynamic characteristics of objects under impact operates as follows.

In a collision of two bodies, when the mass of one body is much larger than the mass of the other, the impact pulse is converted by the transducer 1 into an electric signal. The shape of this signal is an exact replica of the mechanical impulse caused by the impact momentum. The electric signal from the output of the transducer 1 is fed to the pulse shaper 2, where it is shaped into a monopolar signal, amplified and through the conducting switch 3 is fed simultaneously to the inputs of the area measuring unit 7, integrator 8, logical elements AND-NOT 9 and 10 and to the control input of the switch 6. As the impact pulse rises up to the maximum value, the unit 7 measures the area of the leading edge of the pulse. At the same time, the data of the area of the leading edge is recorded into the memory block 13 through the conducting switch 4. With a zero level at the input of the switches 4, 5, and 6, the latter are rendered conductive. The zero level at the input of the switch 4 during the rise of the impact pulse is provided by the logical element AND-NOT 10 whose output is connected to the control input of the switch 4. At the same time, the output of the logical element AND-NOT 10 is connected to the control input of the switch 5 through a logical element NOT and, therefore, during the rise of the impact pulse a non-zero level is applied to the control input of the switch 5 and the switch 5 is rendered nonconductive. The information from the output of the unit 7 during the measurement of the area of the leading edge of the impact pulse does not pass to the memory block 14.

When the signal at the output of the switch 3 rises up during the measurement of the area of the leading edge of the impact pulse, this signal is simultaneously integrated by the integrator 8, at the output of which there is a signal differing from zero. The switch 6 is rendered nonconductive, no signal is present at its output and the trigger 12 is not excited.

When the input signal attains its maximum value, the voltage of the signal at the output of the integrator 8 drops to zero. In this case at the output of the logical element AND-NOT 10 a signal voltage appears, which is different from the zero level, the switch 4 is rendered nonconductive and a signal with zero level appears at the input of the switch 5. The switch 5 is rendered conductive and the data on the area of the trailing edge of the impact pulse is recorded in the memory block 14. Since at this instant of time the switch 4 is rendered nonconductive, the transmission of information to the memory block 13 ceases. During the measurement of the area of the trailing edge of the impact pulse, a zero-level signal appears at the output of the logical element AND-NOT and, in spite of the fact that during this time the switch 6 is rendered conductive, no signal appears at its output and the trigger 12 remains unexcited.

After the action of the impact pulse has ceased, a signal with zero level from the switch 3 and a signal with zero level are applied to one input of the logical element AND-NOT 10. In this case a signal with a non-zero level is applied to the control input of the switch 5, the switch 5 is rendered nonconductive and the memory block 14 stops receiving information on the area of the trailing edge of the pulse. At the same time, at the output of the logical element AND-NOT 9 a digital signal appears whose level differs from zero.

This signal passes through the conducting switch 6, excites the trigger 12, and renders the switch 3 nonconducting thus cutting off the information on jarring and other noise. The trigger 12, produces counting pulses, which are fed to the memory blocks 13 and 14 and allow reading off the information on the leading and trailing edges of the impact pulse. The signals from the outputs of the memory blocks 13, 14 are squared in the squarers 15 and 16 and are applied to the adder 17. The difference of the squared signals proportional to the area of the leading and trailing edges of the impact pulse is equal to the work of plastic deformation caused by the impact to the accuracy of the scale proportionality factor and this magnitude is indicated on the indicator 18. The scale factors are set in the memory blocks 13, 14 during the calibration of the device.

Industrial Application

The device for measuring the dynamic characteristics of objects under impact may successfully be used in the development of shock absorbers, dampers and for development of equistrong members during the impact tests.

We claim:

1. A device for measuring the dynamic characteristics of objects under impact, comprising:
   a transducer responding to the parameters of motion of the object during the impact;
   a pulse shaper the input of which is connected to the output of said transducer;
   a controlled switch having first and second inputs and an output, said first input of which is connected to the output of said pulse shaper;
   a unit with an input and an output and adapted for measuring the area of the impact pulse the input of which is connected to the output of said controlled switch;
   an integrator having an input and an output, the input of which is connected to the output of said controlled switch;
   a first logical AND-NOT element having first and second inputs and an output, said first input thereof being connected to the output of said controlled switch and said second input being connected to the output of said integrator;
   a second logical AND-NOT element having first and second inputs and an output, said first input thereof being connected to the output of said controlled switch and said second input being connected to the output of said integrator;
   a logical NOT element having an input connected to the output of said first logical AND-NOT element;
   a first additional switch having first and second inputs and an output, said first input thereof being connected to the output of said unit for measuring the area of the impact pulse and said second input thereof being connected to the output of said first logical AND-NOT element;
   a second additional switch having a first input, a second input and an output, said first input thereof being connected to the output of said unit for measuring the area of the impact pulse and said second input thereof being connected to the output of said logical NOT element;
   a third additional switch having first and second inputs and an output, said first input thereof being connected to the output of said controlled switch and said second input thereof being connected to the output of said second logical AND-NOT element, and said output thereof being connected to the second input of said controlled switch;
   a first memory block having first and second inputs and an output, one of said inputs of which is connected to the output of said first additional switch;
   a second memory block having first and second inputs and an output, one of said inputs of which is connected to the output of said second additional switch;
   a trigger having an input and first and second outputs, said input of which is connected to the output of said third additional switch and the first output of which is connected to the second input of said first memory block and the second output of which is connected to the second input of said second memory block;
   a first squarer having an input and an output, the input of which is connected to the output of said first memory block;
   a second squarer having an input and an output, the input of which is connected to the output of said second memory block;
   an adder having two inputs and an output, the inputs of which are connected to the outputs of said first and second squarers; and
   an indicator having an input connected to the output of said adder.

* * * * *